(12) United States Patent
Jiaang et al.

(10) Patent No.: US 8,071,787 B2
(45) Date of Patent: Dec. 6, 2011

(54) PYRROLIDINE COMPOUNDS

(75) Inventors: Weir-Tong Jiaang, Taichung (TW); Xin Chen, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 12/708,997

(22) Filed: Feb. 19, 2010

(65) Prior Publication Data
US 2010/0234431 A1    Sep. 16, 2010

Related U.S. Application Data

(60) Provisional application No. 61/159,993, filed on Mar. 13, 2009.

(51) Int. Cl.
*C07D 295/00*   (2006.01)

(52) U.S. Cl. ........ 548/530; 544/350; 544/372; 546/114; 546/208; 546/276.4; 548/146; 548/470

(58) Field of Classification Search .................. 544/350, 544/372; 546/114, 208, 276; 548/146, 470, 548/530
See application file for complete search history.

(56) References Cited

OTHER PUBLICATIONS

Kanemasa, et al. Chem. Lett., 9, 1992, 1801-1804.*
Tran, Thuy, et al. "Synthesis and structure-activity relationship of N-acyl-Gly-, N-acyl-Sar- and N-blocked-boroPro inhibitors of FAP, DPP4, and POP" *Bioorganic & Medicinal Chemistry Letters 17* (2007) pp. 1438-1442.
Hu, Yi, et al. "Synthesis and structure-activity relationship of N-alkyl Gly-boro-Pro inhibitors of DPP4, FAP, and DPP7" *Bioorganic & Medicinal Chemistry Letters 15* (2005) pp. 4239-4242.

* cited by examiner

*Primary Examiner* — James O Wilson
*Assistant Examiner* — Douglas M Willis
(74) *Attorney, Agent, or Firm* — Occhiuti Rohlicek & Tsao LLP

(57) ABSTRACT

A compound of the following formula:

wherein $R_1$, $R_2$, $R_3$, $R_4$, $R_5$, $R_6$, $R_7$, $R_8$, $R_9$, $R_{10}$, $R_{11}$, $R_{12}$, X, Y, and Z are as defined herein. Also disclosed is a method for inhibiting actively of fibroblast activation protein or for treating cancer or inflammation conditions with such a compound.

19 Claims, No Drawings

PYRROLIDINE COMPOUNDS

CROSS REFERENCE TO RELATED APPLICATIONS

This application claims priority to U.S. Provisional Application Ser. No. 61/159,993, both filed Mar. 13, 2009. The contents of the prior application are hereby incorporated by reference in their entireties.

BACKGROUND

Dipeptidyl peptidases, enzymes that catalyze the hydrolysis of polypeptides to release dipeptides, play important roles in physiological and pathological processes. Dipeptidyl peptidases IV (DPP-IV) and fibroblast activation protein (FAP) are two well-known members of the dipeptidyl peptidases family.

DPP-IV degrades glucagon-like peptide-1 and glucose-dependent insulinotropic polypeptide hormones produced by intestinal endocrine L-cells in response to nutrient ingestion. Inhibiting DPP-IV enhances insulin secretion, lowers blood sugar levels, and improves pancreatic β-cell function. Deacon C. et al., *Expert Opin. Investig. Drugs* 2007 16: 533-545 and Deacon C. *Curr. Opin. Investig. Drugs* 2008, 9: 402-413. The DPP-IV inhibition is well tolerated and does not cause hypoglycemia or increase body weight in human. Deacon C. *Curr. Opin. Investig. Drugs* 2008, 9: 402-413 and Rosenstock J. et al., *Diabetes Obes. Metab.* 2008, 10: 376-386. Thus, inhibitors of DPP-IV are potential drug candidates for type-II diabetes. See, e.g., Pederson R. et al., *Diabetes* 1998, 47: 1253-1258; Ahren B. et al., *Diabetes Care* 2002, 25: 869-875; Deacon C. et al., *Expert Opin. Investig. Drugs* 2004, 13:1091-1102; and Pei Z. *Curr. Opin. Drug Discov. Devel.* 2008, 11: 512-532.

FAP is exclusively expressed in fetal cells, wounded tissue, and stromal fibroblasts in most malignant epithelial tumors. See Scanlan M. et al., *Proc. Natl. Acad. Sci. U.S.A* 1994, 91: 5657-5661; Rettig W. et al., *Proc. Natl. Acad. Sci. U.S.A* 1988, 85: 3110-3114; and Huber M. et al., *J. Invest. Dermatol.* 200, 120: 182-188. Studies show that xenografted mice with constitutively expressed FAP were 2-4 folds more likely to develop tumors than the mock-transfection and demonstrated 10-40 fold tumor growth than the control mice. See Cheng J. et al., *Cancer Res.* 2002, 62: 4767-4772. When the xenografted mice were treated with anti-FAP antisera, the tumor growth was attenuated. Human clinical trials show that patients whose colon tumors had high levels of stromal FAP were more likely to have aggressive disease progression and potential development of metastases or recurrence. See Henry L. et al., *Clin. Cancer Res.* 2007, 13: 1736-1741. Thus, anti-FAP agents can be used to treat cancers.

In addition, FAP is also highly expressed in fibroblast-like synoviocytes from rheumatoid arthritis (RA) and osteroarthritis (OA) patients. Bauer S. et al., *Arthritis Res. Ther.* 2006, 8: R171. It is therefore suggested using FAP as a therapeutic target to treat RA or OA.

SUMMARY

This invention is based on an unexpected finding that a group of bicyclic diamide compounds effectively inhibited dipeptidyl peptidase activity. One aspect of this invention relates to bicyclic diamide compounds of the following formula:

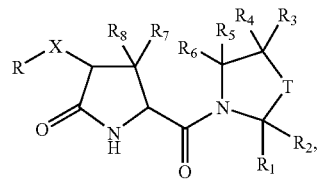

wherein each of $R_1$, $R_2$, $R_3$, $R_4$, $R_5$, $R_6$, $R_7$, and $R_8$, independently, is H, halo, alkyl, cyano, nitro, amino, boronic acid, boronic ester, cycloalkyl, heterocycloalkyl, aryl, or heteroaryl; T is $C(R_aR_b)$, $NR_c$, O, or S; in which each of $R_a$ and $R_b$, independently, is H, alkyl, halo, cyano, nitro, amino, alkoxyl, hydroxyl, cycloalkyl, heterocycloalkyl, aryl, or heteroaryl; and $R_c$ is H, alkyl, cycloalkyl, heterocycloalkyl, aryl, or heteroaryl; X is $C(R_dR_e)$, $NR_f$, O, S, or deleted; in which each of $R_d$ and $R_e$, independently, is H, alkyl, halo, cyano, nitro, alkoxyl, hydroxyl, cycloalkyl, heterocycloalkyl, aryl, or heteroaryl; and $R_f$ is H, alkyl, cycloalkyl, heterocycloalkyl, aryl, or heteroaryl; and $R_f$ is alkyl, cycloalkyl, heterocycloalkyl, aryl, heteroaryl, —C(O)$OR_g$, or —C(O)$NR_hR_i$; in which $R_g$ is alkyl, cycloalkyl, heterocycloalkyl, aryl, heteroaryl; and each of $R_h$ and $R_i$ independently, is H, alkyl, cycloalkyl, heterocycloalkyl, aryl, heteroaryl, arylalkyl, or hydroxyl, or $R_h$ and $R_i$ together with the N atom to which they are attached form a 5 or 6 membered ring, optionally substituted with alkyl, aryl, halo, hydroxyl, alkyloxyl, nitro, amino, alkoxycarbonyl, or carboxy; and optionally fused with a 3-8 membered aromatic or non-aromatic ring containing 0, 1, 2, or 3 heteroatoms.

Referring to the above formula, a subset of the above-described compounds feature that T is $CH_2$ or S, X is $CH_2$ or deleted, R is —C(O)$NR_hR_i$; $R_h$ and $R_i$ together with the N atom to which they are attached form a 5 or 6 membered ring, optionally substituted with alkyl, aryl, halo, hydroxyl, alkyloxyl, nitro, amino, alkoxycarbonyl, or carboxy; and optionally fused with a 3-8 membered aromatic or non-aromatic ring containing 0, 1, 2, or 3 heteroatoms. Another subset of the compounds feature that R is —C(O)$NR_hR_i$; each of $R_h$ and $R_i$, independently, is H, alkyl, cycloalkyl, heterocycloalkyl, aryl, heteroaryl, arylalkyl, or hydroxyl.

Shown below are exemplary compounds related to this invention:

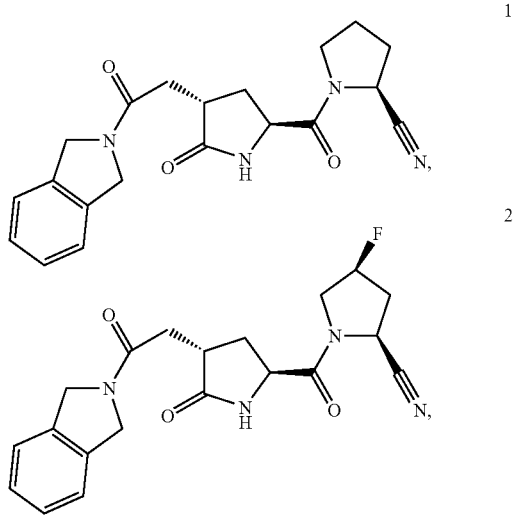

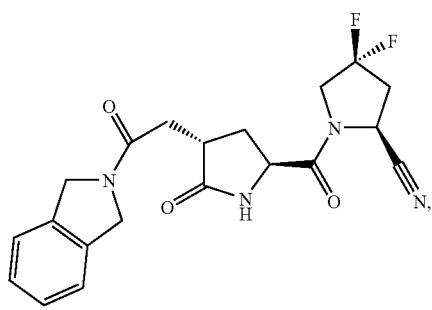
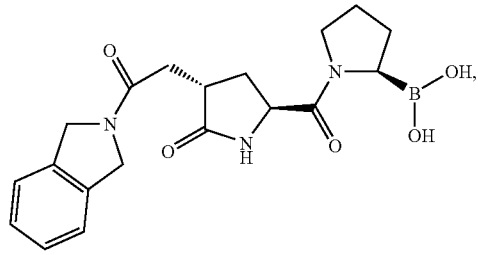
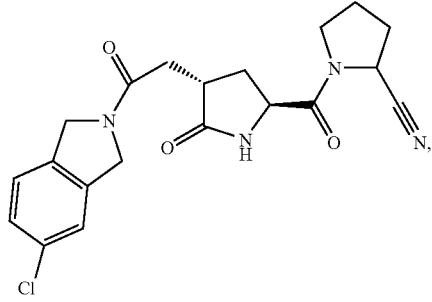
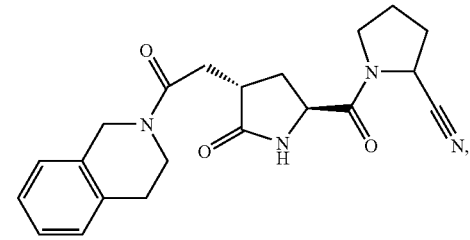
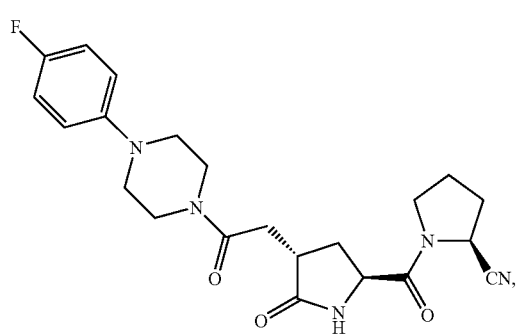
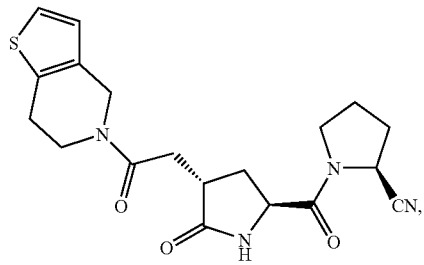
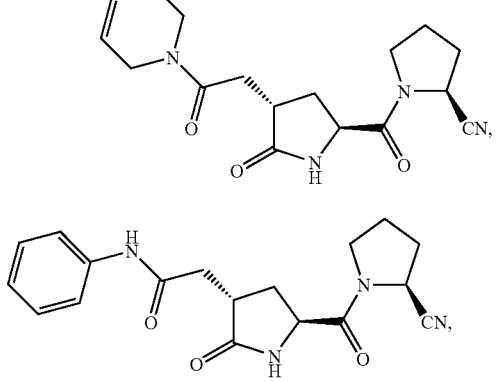
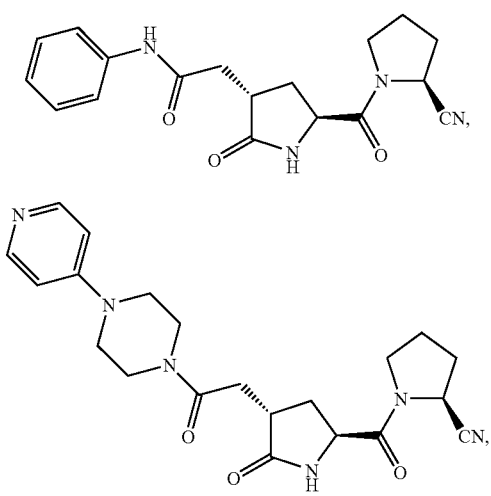
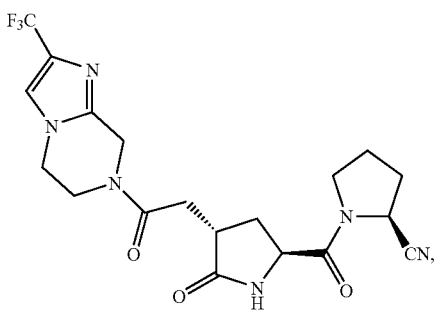
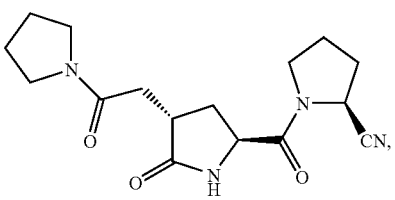

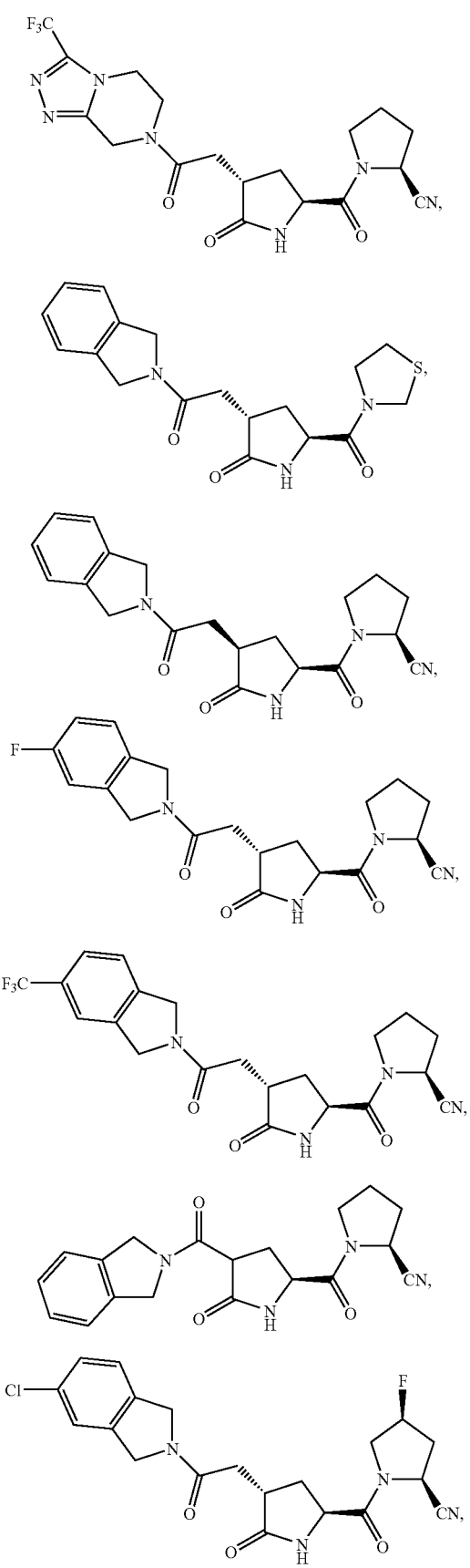

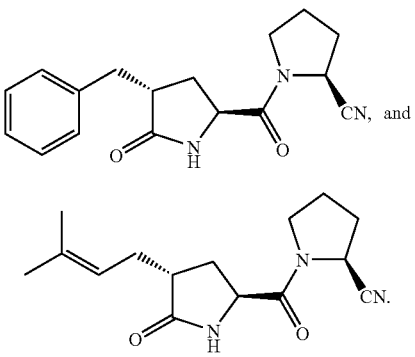

The term "alkyl" herein refers to a straight or branched hydrocarbon, containing 1-10 carbon atoms. Examples of alkyl groups include, but are not limited to, methyl, ethyl, n-propyl, i-propyl, n-butyl, i-butyl, and t-butyl. The term "alkoxy" refers to an —O-alkyl. The term "alkoxyalkyl" refers to an alkyl group substituted with one or more alkoxy groups. The term "haloalkyl" refers to an alkyl group substituted with one or more halo groups. The term "hydroxyalkyl" refers to an alkyl group substituted with one or more hydroxy groups.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl. The term "aryloxy" refers to an —O-aryl moiety. The term "aralkyl" refers to an alkyl group substituted with an aryl group.

The term "cycloalkyl" refers to a saturated and partially unsaturated cyclic hydrocarbon group having 3 to 12 carbons. Examples of cycloalkyl groups include, but are not limited to, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having one or more heteroatoms (such as O, N, or S). Examples of heteroaryl groups include pyridyl, furyl, imidazolyl, benzimidazolyl, pyrimidinyl, thienyl, quinolinyl, indolyl, and thiazolyl. The term "heteroaralkyl" refers to an alkyl group substituted with a heteroaryl group.

The term "heterocycloalkyl" refers to a nonaromatic 5-8 membered monocyclic, 8-12 membered bicyclic, or 11-14 membered tricyclic ring system having one or more heteroatoms (such as O, N, or S). Examples of heterocycloalkyl groups include, but are not limited to, piperazinyl, pyrrolidinyl, dioxanyl, morpholinyl, and tetrahydrofuranyl.

The term "boronic acid" refers to a group of —B(OH)$_2$. The term "boronic ester" refers to a group of —B(OH)(OR) or —B(OR)(OR'). Each of R and R', independently, is alkyl, aryl, heteroaryl, cycloalkyl, or heterocyclo; or R and R' together are alkylene. Examples of boronic ester include

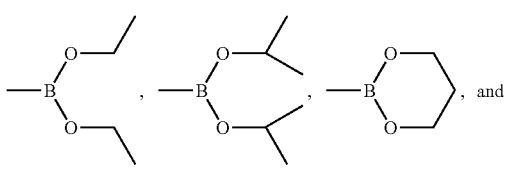

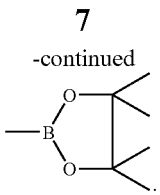

Alkyl, cycloalkyl, heterocycloalkyl, aryl, heteroaryl, aralkyl, heteroaralkyl, alkoxy, and aryloxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, heterocycloalkyl, in which alkyl, alkenyl, alkynyl, alkyloxy, aryl, heteroaryl cycloalkyl, and heterocycloalkyl may further substituted.

The diamide compounds described above include their pharmaceutically acceptable salts and prodrugs, if applicable. Such a salt can be formed between a positively charged ionic group in a diamide compound (e.g., ammonium) and a negatively charged counterion (e.g., trifluoroacetate). Likewise, a negatively charged ionic group in a diamide compound (e.g., carboxylate) can also form a salt with a positively charged counterion (e.g., sodium, potassium, calcium, or magnesium). The diamide compounds may contain a non-aromatic double bond and one or more asymmetric centers. Thus, they can occur as racemic mixtures, single enantiomers, individual diastereomers, diastereomeric mixtures, and cis- or trans-isomeric forms. All such isomeric forms are contemplated.

Another aspect of this invention relates to a method of using one of above-described diamide compounds to inhibit activity of dipeptidyl peptidase (e.g., DPP-IV or FAP) or treat cancer or an inflammation condition.

Also within the scope of this invention is a pharmaceutical composition containing one or more of the above-described diamide compounds and a pharmaceutically acceptable carrier, as well as use of the composition for the manufacture of a medicament for treating cancer or inflammation.

The details of many embodiments of the invention are set forth in the description below. Other features, objects, and advantages of the invention will be apparent from the description and the claims.

DETAILED DESCRIPTION

The diamide compounds of this invention can be prepared by synthetic methods well known in the art. An exemplary synthetic route is shown in Scheme 1 below.

Scheme 1

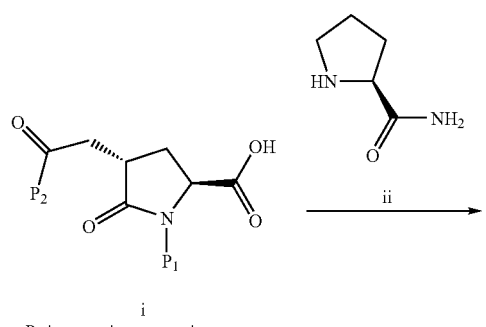

$P_1$ is an amino protecting group
$P_2$ is an acid protecting group

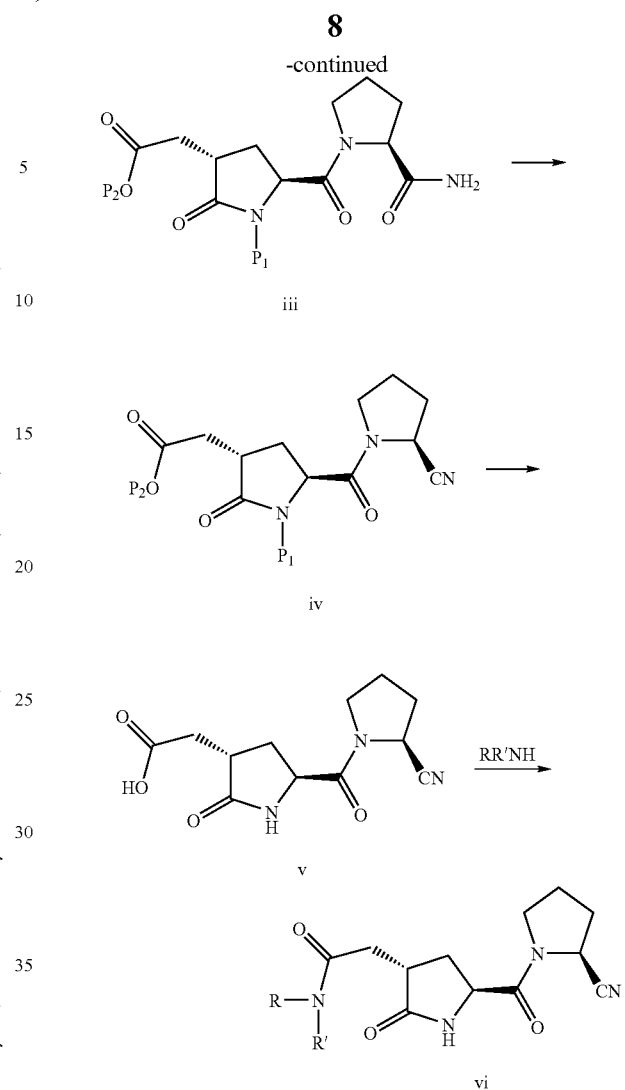

The starting compound pyrrolidine-2-one compound (I) has a protected amino group and a protected 4-methylcarboxy group. It can be prepared by methods well known in the art. See, e.g., *Tetrahedron Lett.* 1988, 39, 2199-2202; *J. Chem. Soc. Perkin Trans. I*, 2002, 613-621; *J. Chem. Soc. Perkin Trans. I*, 2001, 2361-2371; and *J. Org. Chem.* 1994, 59, 4327-4331. Compound (I) is reacted with commercially available L-prolinamide (ii) to give 5-oxopyrrolidine-2-carbonylpyrrolidine-2-carboxamide (iii), dehydration of which transforms the 2-carboxamide group to a cyano group to produce compound (iv). Compound (iv) is then subjected to deprotection to remove the amino and acid protecting groups to produce compound (v), coupling of which with an amino compound affords compound (vi), a compound of this invention.

The diamide compounds thus synthesized can be further purified by column chromatography, high performance liquid chromatography, or crystallization.

The above scheme demonstrates a method of synthesizing a specific diamide compound of this invention. A skilled person in the art can modify the method to synthesize other diamide compounds of this invention. Alternatively, he or she may use other methods well known in the art to synthesize the diamide compounds of this invention.

Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The diamide compounds of this invention show effective inhibition against dipeptidyl peptidase, e.g., DPP-IV and FAP. Thus, this invention relates to a method of inhibiting dipeptidyl peptidase by contacting the enzyme with an effective amount of one or more diamide compounds. Also included in this invention is a method of treating cancer or an inflammation condition by administering to a subject who needs the treatment an effective amount of one or more of the diamide compounds described above. The term "treating" refers to application or administration of the diamide compound to a subject, who has cancer or inflammation, a symptom of cancer or inflammation conditions, or a predisposition toward cancer or inflammation, with the purpose to cure, heal, alleviate, relieve, alter, remedy, ameliorate, improve, or affect the disease, the symptom, or the predisposition. "An effective amount" refers to the amount of the diamide compound which is required to confer the desired effect on the subject. Effective amounts vary, as recognized by those skilled in the art, depending on route of administration, excipient usage, and the possibility of co-usage with other therapeutic treatments such as use of other active agents.

Cancer is a class of diseases in which a group of cells having the capacity for autonomous growth, i.e., an abnormal state or condition characterized by rapidly proliferating cell growth and sometimes tumor metastasis. Examples of cancers include, but are not limited to, carcinoma and sarcoma such as leukemia, sarcomas, osteosarcoma, lymphomas, melanoma, ovarian cancer, skin cancer, testicular cancer, gastric cancer, pancreatic cancer, renal cancer, breast cancer, prostate colorectal cancer, cancer of head and neck, brain cancer, esophageal cancer, bladder cancer, adrenal cortical cancer, lung cancer, bronchus cancer, endometrial cancer, nasopharyngeal cancer, cervical or hepatic cancer, colon cancer, kidney cancer, thyroid cancer, haematopoietic cancer, and cancer of unknown primary site.

Inflammation conditions include, but are not limited to, asthma, adult respiratory distress syndrome, diabetes (e.g., type-II diabetes), infant respiratory distress syndrome, osteoarthritis, rheumatoid arthritis, inflammatory bowel disease, psoriasis, and dermatitis.

To treat cancer or inflammation, a composition having one or more of the diamide compounds described above can be administered to a subject in need of such treatment parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acids, such as oleic acid and its glyceride derivatives, are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having an active diamide compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active diamide compound. Examples of other carriers include colloidal silicon oxide, magnesium stearate, cellulose, sodium lauryl sulfate, and D&C Yellow # 10.

The diamide compounds of this invention can be preliminarily screened by an in vitro assay for one or more of their desired activities, e.g., inhibiting DPP-IV or FAP activity. Compounds that demonstrate high activities in the preliminary screening can further be screened for their efficacy by in vivo assays. For example, a test compound can be administered to an animal (e.g., a mouse model) having cancer or inflammation and its therapeutic effect is then accessed. Based on the results, an appropriate dosage range and administration route can also be determined.

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

All of the publications, including patents, cited herein are hereby incorporated by reference in their entirety.

Example 1

Preparation of (2S)-1-({(2S,4S)-4-[2-(1,3-dihydro-2H-isoindol-2-yl)-2-oxoethyl]-5-oxopyrrolidin-2-yl}carbonyl)pyrrolidine-2-carbonitrile (compound 1)

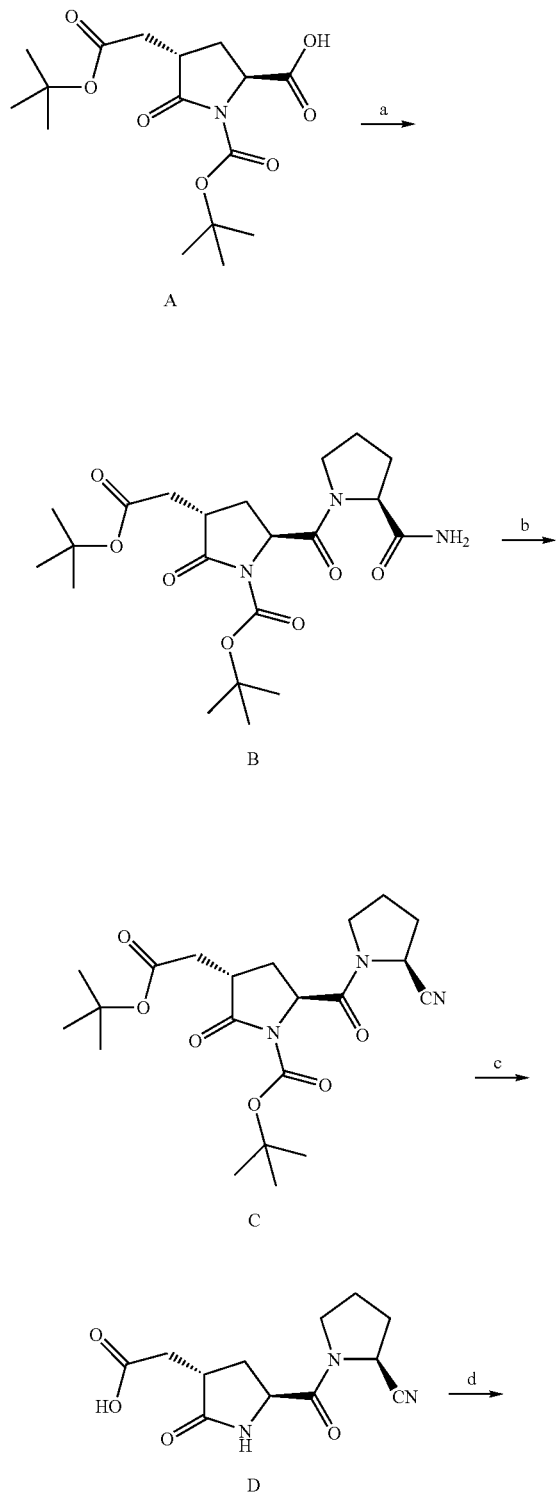

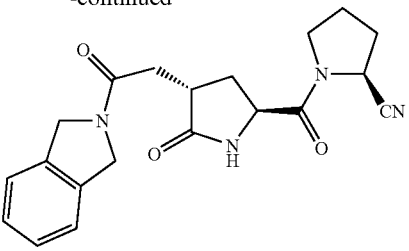

Reagents: (a) EDC, HOBt, 1,4-dioxane/CH$_2$Cl$_2$, L-prolinamide;
(b) imidazole, POCl$_3$, pyridine; (c) CF$_3$COOH, CH$_3$CN;
(d) EDC, HOBt, 1,4-dioxane/CH$_2$Cl$_2$, isoindoline (2S,4S)-1-(tert-butoxycarbonyl)-4-(2-tert-butoxy-2-oxoethyl)-5-oxopyrrolidine-2-carboxylic acid was prepared according to the method described in *Tetrahedron Lett.* 1988, 39, 2199-2202. To a solution containing this compound (343 mg, 1.0 mmol) and N-hydroxybenzotrizole (HOBt, 168 mg, 1.1 mmol) in 1,4-dioxane (5 mL) was added a solution of 1-ethyl-3-(3-dimethylaminopropyl) carbodiimide (EDC, 211 mg, 1.1 mmol) in CH$_2$Cl$_2$ (5 mL). The mixture was stirred for 10 min at room temperature. (S)-Pyrrolidine-2-carboxamide (125 mg, 1.1 mmol) in CH$_2$Cl$_2$ (4 mL) was added with stirring. After 16 h, the reaction mixture was washed with saturated aqueous NaHCO$_3$ solution (10 mL), 1 N aqueous citric acid solution (10 mL), and brine (10 mL). The combined organic layers were dried over MgSO$_4$, filtered, and concentrated. The resulting residue was purified over silica gel using CH$_2$Cl$_2$/MeOH (95:5) as an eluant to yield compound A (347 mg, 0.79 mmol, 79%).

To the mixture of tent-butyl (3S,5S)-5-{[(2S)-2-carbamoylpyrrolidin-1-yl]carbonyl}-3-(2-tert-butoxy-2-oxoethyl)-2-oxopyrrolidine-1-carboxylate (347 mg, 0.79 mmol), imidazole (80 mg, 1.18 mmol), and pyridine (7 ml) at −30° C. was added phosphoryl chloride (484 mg, 3.16 mmol) dropwise over 5 min. The resulting cloudy white reaction mixture was turned to a slight yellowish opaque suspension after stirred for 1 h at −30° C. It was concentrated under vacuum, diluted with CH$_2$Cl$_2$, and treated with 1 N aqueous citric acid solution (5 mL). The organic layer was dried over MgSO$_4$, filtered, and concentrated. The resulting residue was purified over silica gel using Hexane/EtOAc (1:2) as an eluent to yield the desired compound B (286 mg, 0.68 mmol, 86%).

To a solution of tent-butyl (3S,5S)-5-{[(2S)-2-cyanopyrrolidin-1-yl]carbonyl}-3-(2-tert-butoxy-2-oxoethyl)-2-oxopyrrolidine-1-carboxylate (286 mg, 0.68 mmol) in CH$_3$CN (5 ml) at 0° C. was added TFA 5 ml dropwise over 5 min. The reaction mixture was stirred for 1 h at room temperature. The reaction mixture was concentrated under vacuum and crystallized with EA/ethr to yield compound C.

To a stirred solution of [(3S,5S)-5-{[(2S)-2-cyanopyrrolidin-1-yl]carbonyl}-2-oxopyrrolidin-3-yl]acetic acid (265 mg, 0.50 mmol) and HOBt (42 mg, 0.55 mmol) in 1,4-dioxane (3 mL) was added a solution of EDC (105 mg, 0.55 mmol) in CH$_2$Cl$_2$ (3 mL). The mixture was stirred for 10 min at room temperature. Isoindoline (65 mg, 0.55 mmol) in CH$_2$Cl$_2$ (2 mL) was added with stirring. After 16 h, the reaction mixture was washed with saturated aqueous NaHCO$_3$ (10 mL), 1 N aqueous citric acid (10 mL), and brine (10 mL). The organic layers were dried over MgSO$_4$, filtered, and concentrated. The residue was purified over silica gel using CH$_2$Cl$_2$/MeOH (98:2) as an eluent to yield compound 1 (128 mg, 0.35 mmol, 70%). $^1$H NMR (300 MHz, CDCl$_3$): (6/1 mixture of trans/cis amide rotomers) δ 7.30-7.26 (m, 4H), 6.56 (s, 0.86H), 6.06 (s, 0.14H), 4.82-4.77 (m, 4.86H, overlapped two singlet at 4.82, 4.77), 4.60 (d, J=6.6 Hz, 0.14H), 4.55 (d, J=9.0 Hz, 0.14H), 4.40 (dd, J=3.0, 9.0 Hz, 0.86H), 3.61-3.04 (m, 2H), 3.02-2.88 (m, 2H), 2.68-2.36 (m, 3H), 2.29-2.12 (m, 4H). MS (ES$^+$) m/z calcd. for $C_{20}H_{22}N_4O_3$: 366.17. found: 367.1 (M+H).

Example 2

Preparation of (2S,4S)-1-({(2S,4S)-4-[2-(1,3-dihydro-2H-isoindol-2-yl)-2-oxoethyl]-5-oxopyrrolidin-2-yl}carbonyl)-4-fluoropyrrolidine-2-carbonitrile (compound 2)

The title compound was prepared in a manner similar to that described in Example 1.

$^1$H NMR (300 MHz, CDCl$_3$): (7/1 mixture of trans/cis amide rotamers) δ 7.28-7.25 (m, 4H), 7.23 (s, 0.88H), 6.28 (s, 0.12H), 5.54 (brs, 0.44H), 5.46 (brs, 0.06H), 5.36 (brs, 0.44H), 5.30 (brs, 0.06H), 5.09 (d, J=8.4 Hz, 0.88H), 4.84 (d, J=8.4 Hz, 0.12H), 4.80 (s, 2H), 4.75 (s, 2H), 4.57 (d, J=8.4 Hz, 0.12H), 4.38 (d, J=8.4 Hz, 0.88H), 3.39-3.76 (m, 2H), 3.02-2.78 (m, 2H), 2.67-2.25 (m, 5H). MS (ES$^+$) m/z calcd. for $C_{20}H_{21}FN_4O_3$: 384.16. found: 385.0 (M+H).

Example 3

Preparation of (2S)-1-({(2S,4S)-4-[2-(1,3-dihydro-2H-isoindol-2-yl)-2-oxoethyl]-5-oxopyrrolidin-2-yl}carbonyl)-4,4-difluoropyrrolidine-2-carbonitrile (compound 3)

The title compound was prepared in a manner similar to that described in Example 1.

$^1$H NMR (300 MHz, DMSO-d$_6$): (6/1 mixture of trans/cis amide rotamers) δ 8.03 (s, 0.86H), 7.97 (s, 0.14H), 7.36-7.25 (m, 4H), 5.37 (d, J=8.4 Hz, 0.14H), 5.09 (dd, J=4.2, 8.4 Hz, 0.86H), 4.82 (s, 2H), 4.62 (s, 2H), 4.32 (d, J=8.7 Hz, 1H), 4.25-4.04 (m, 2H), 2.93-2.66 (m, 4H), 2.49-2.05 (m, 3H). MS (ES$^+$) m/z calcd. for $C_{20}H_{20}F_2N_4O_3$: 402.15. found: 403.1 (M+H).

Example 4

Preparation of (2S)-1-({(2S,4S)-4-[2-(1,3-dihydro-2H-isoindol-2-yl)-2-oxoethyl]-5-oxopyrrolidin-2-yl}carbonyl)pyrrolidine-2-boronic acid (compound 4)

The title compound was prepared in a manner similar to that described in Example 1.

$^1$H NMR (400 MHz, D$_2$O): (4/1 mixture of trans/cis amide rotamers) δ 7.19-7.17 (m, 4H), 4.69-4.61 (m, 2H), 4.43 (d, J=6.4 Hz, 0.8H), 4.24 (d, J=6.4 Hz, 0.2H), 3.65-3.55 (m, 1H), 3.39-3.31 (m, 1H), 3.19 (s, 2H), 3.06-3.02 (m, 1H), 2.91-2.72 (m, 2H), 2.53-2.49 (m, 1H), 2.37-2.21 (m, 2H), 2.01-1.86 (m, 3H), 1.62-1.56 (m, 1H).

Example 5

Preparation of (2S)-1-({(2S,4S)-4-[2-(5-chloro-1,3-dihydro-2H-isoindol-2-yl)-2-oxoethyl]-5-oxopyrrolidin-2-yl}carbonyl)pyrrolidine-2-carbonitrile (compound 5)

The title compound was prepared in a manner similar to that described in Example 1.

$^1$H NMR (300 MHz, CDCl$_3$): (7/1 mixture of trans/cis amide rotamers) δ 7.37-7.18 (m, 3.88H), 6.56 (s, 0.12H), 5.31-4.69 (m, 5H), 4.53 (d, J=9.3 Hz, 0.12H), 4.42 (dd, J=2.1, 9.3 Hz, 0.88H), 3.61-3.57 (m, 2H), 3.01-2.87 (m, 2H), 2.57-2.18 (m, 7H). MS (ES$^+$) m/z calcd. for $C_{20}H_{21}ClN_4O_3$: 400.13. found: 400.9 (M+H), 402.9 (M+2).

Example 6

Preparation of (2S)-1-({(2S,4S)-4-[2-(1,3-dihydro-2H-isoquinol-2-yl)-2-oxoethyl]-5-oxopyrrolidin-2-yl}carbonyl)pyrrolidine-2-carbonitrile (compound 6)

The title compound was prepared in a manner similar to that described in Example 1.

$^1$H NMR (300 MHz, CDCl$_3$): (7/1 mixture of trans/cis amide rotamers) δ 7.28-7.12 (m, 4.88H), 6.54 (s, 0.12H), 4.84 (t like, J=5.1 Hz, 1H), 4.63 (s, 1H), 4.62 (s, 1H), 4.49 (d, J=9.3 Hz, 0.12H), 4.38 (d, J=9.3 Hz, 0.88H), 3.81-3.66 (m, 2H), 3.57-3.53 (m, 2H), 3.00-2.82 (m, 4H), 2.57-2.15 (m, 7H). MS (ES$^+$) m/z calcd. for $C_{20}H_{24}N_4O_3$: 380.18. found: 381.0 (M+H).

Example 7

Preparation of (2S)-1-({(2S,4S)-4-[2-[4-(4-Fluorophenyl)-piperazin-1-yl]-2-oxoethyl]-5-oxopyrrolidin-2-yl}carbonyl)pyrrolidine-2-carbonitrile (compound 7)

The title compound was prepared in a manner similar to that described in Example 1.

$^1$H NMR (300 MHz, CDCl$_3$): (7/1 mixture of trans/cis amide rotamers) δ 7.27-6.85 (m, 4.88H), 6.27 (s, 0.12H), 4.83-4.82 (m, 0.88H), 4.60 (d, J=6.6 Hz, 0.12H), 4.48 (d, J=8.4 Hz, 0.12H), 4.36 (d, J=8.4 Hz, 0.88H), 3.80-3.55 (m, 6H), 3.10-2.91 (m, 6H), 2.56-2.47 (m, 2H), 2.38-2.17 (m, 7H). MS (ES$^+$) m/z calcd. for $C_{22}H_{26}FN_5O_3$: 427.20. found: 428.0 (M+H).

Example 8

Preparation of (2S)-1-({(2S,4S)-4-[2-(6,7-dihydrothieno[3,2-c]pyridin-5(4H)-yl)-2-oxoethyl]-5-oxopyrrolidin-2-yl}carbonyl)pyrrolidine-2-carbonitrile (compound 8)

The title compound was prepared in a manner similar to that described in Example 1.

$^1$H NMR (300 MHz, CDCl$_3$): (8/1 mixture of trans/cis amide rotamers) δ 7.14 (t, J=5.4 Hz, 1H), 6.88 (d, J=5.4 Hz, 0.89H), 6.79 (dd, J=3.3, 5.4 Hz, 1H), 6.43 (d, J=5.4 Hz, 0.11H), 4.82-4.80 (m, 0.89H), 4.72-4.44 (m, 2.22H, overlapped two singlet at 4.64, 4.56), 4.36 (d, J=9.6 Hz, 0.89H), 3.96-3.48 (m, 4H), 3.04-2.83 (m, 4H), 2.62-2.11 (m, 5H). MS (ES$^+$) m/z calcd. for $C_{19}H_{22}N_4O_3S$: 386.14. found: 386.9 (M+H).

Example 9

Preparation of (2S)-1-({(2S,4S)-4-[2-[4-(4-chlorophenyl)-3,6-dihydropyridin-1(2H)-yl]-2-oxoethyl]-5-oxopyrrolidin-2-yl}carbonyl)pyrrolidine-2-carbonitrile (compound 9)

The title compound was prepared in a manner similar to that described in Example 1.

$^1$H NMR (300 MHz, CDCl$_3$): (9/1 mixture of trans/cis amide rotamers) δ 7.30 (s, 4H), 6.80 (d, J=3.9 Hz, 0.9H), 6.19 (s, 0.1H), 6.06 (brs, 0.5H), 5.99 (brs, 0.5H), 4.83-4.81 (m, 0.9H), 4.60 (d, J=6.9 Hz, 0.1H), 4.58 (d, J=9.3 Hz, 0.1H), 4.36 (dd, J=2.4, 9.3 Hz, 0.9H), 4.20 (brs, 1H), 4.13 (d, J=2.4 Hz, 1H), 3.82-3.52 (m, 4H), 3.02-2.87 (m, 2H), 2.59-2.46 (m, 4H), 2.39-2.14 (m, 5H). MS (ES⁺) m/z calcd. for $C_{23}H_{25}ClN_4O_3$: 440.16. found: 440.9 (M+H), 442.0 (M+2).

Example 10

Preparation of 2-[(3S,5S)-5-{[(2S)-2-cyanopyrrolidin-1-yl]carbonyl}-2-oxopyrrolidin-3-yl]-N-phenylacetamide (compound 10)

The title compound was prepared in a manner similar to that described in Example 1.

¹H NMR (400 MHz, CDCl₃): (8/1 mixture of trans/cis amide rotamers) δ 8.96 (s, 1H), 7.54 (d, J=7.6 Hz, 2H), 7.32-7.15 (m, 2.89H), 7.06 (t, J=7.6 Hz, 1H), 6.47 (s, 0.11H), 4.75-4.73 (m, 0.89H), 4.61 (d, J=7.6 Hz, 0.11H), 4.49 (d, J=8.8 Hz, 0.11H), 4.33 (dd, J=2.8, 8.8 Hz, 0.89H), 3.50-3.47 (m, 2H), 3.03-2.95 (m, 1H), 2.76 (dd, J=6.4, 15.2 Hz, 1H), 2.52 (dd, J=6.4, 15.2 Hz, 1H), 2.40-2.04 (m, 6H). MS (ES⁺) m/z calcd. for $C_{18}H_{20}N_4O_3$: 340.15. found: 341.0 (M+H).

Example 11

Preparation of (2S)-1-({(2S,4S)-4-[2-[4-(pyridine-4-yl)-piperazin-1-yl]-2-oxoethyl]-5-oxopyrrolidin-2-yl}carbonyl)pyrrolidine-2-carbonitrile (compound 11)

The title compound was prepared in a manner similar to that described in Example 1.

¹H NMR (400 MHz, CDCl₃): (9/1 mixture of trans/cis amide rotamers) δ 8.29 (d, J=5.2 Hz, 2H), 6.95 (s, 0.9H), 6.65 (d, J=5.2 Hz, 2H), 6.39 (s, 0.1H), 4.82-4.80 (m, 0.9H), 4.60 (d, J=8.0 Hz, 0.1H), 4.49 (d, J=8.0 Hz, 0.1H), 4.36 (d, J=8.0 Hz, 0.9H), 3.85-3.48 (m, 6H), 3.45-3.31 (m, 4H), 3.07-2.87 (m, 2H), 2.55-2.16 (m, 7H). MS (ES⁺) m/z calcd. for $C_{21}H_{26}N_6O_3$: 410.21. found: 411.3 (M+H), 433.3 (M+23).

Example 12

Preparation of (2S)-1-({(2S,4S)-5-oxo-4-[2-oxo-[2-(trifluoromethyl)-5,6-dihydroimidazo[1,2-c]pyrazin-7(8H)-yl]ethyl]pyrrolidin-2-yl}carbonyl)pyrrolidine-2-carbonitrile (compound 12)

The title compound was prepared in a manner similar to that described in Example 1.

¹H NMR (400 MHz, CDCl₃): (6/1 mixture of trans/cis amide rotamers) δ 7.22 (d, J=10.0 Hz, 0.86H), 7.08 (s, 1H), 6.58 (d, J=10.0 Hz, 0.14H), 4.94-4.57 (m, 3H), 4.47-4.46 (m, 0.14H), 4.32 (d, J=9.6 Hz, 0.86H), 4.11-3.92 (m, 4H, overlapped singlet at 4.01), 3.61-3.52 (m, 2H), 2.92-2.88 (m, 2H), 2.63-2.54 (m, 1H), 2.42-2.14 (m, 6H). MS (ES⁺) m/z calcd. for $C_{19}H_{21}F_3N_6O_3$: 438.16. found: 439.1 (M+H).

Example 13

Preparation of (2S)-1-({(2S,4S)-5-oxo-4-[2-oxo-2-(pyrrolidin-1-yl)ethyl]pyrrolidin-2-yl}carbonyl)pyrrolidine-2-carbonitrile (compound 13)

The title compound was prepared in a manner similar to that described in Example 1.

¹H NMR (300 MHz, CDCl₃): (13/1 mixture of trans/cis amide rotamers) δ 7.41 (s, 0.93H), 6.74 (s, 0.07H), 4.83-4.80 (m, 0.93H), 4.67 (d, J=4.5 Hz, 0.07H), 4.51 (d, J=7.8 Hz, 0.07H), 4.42 (d, J=7.8 Hz, 0.93H), 4.03 (brs, 1H), 3.60-3.56 (m, 2H), 3.45-3.39 (q like, J=6.3 Hz, 4H), 2.95-2.76 (m, 2H), 2.48-2.15 (m, 6H), 1.99-1.80 (m, 4H). MS (ES⁺) m/z calcd. for $C_{16}H_{22}N_4O_3$: 318.17. found: 319.1 (M+H), 341.1 (M+23).

Example 14

Preparation of (2S)-1-({(2S,4S)-5-oxo-4-[2-oxo-2-[3-(trifluoromethyl)-5,6-dihydro[1,2,4]triazolo[4,3-c]pyrazin-7(8H)-yl]ethyl]pyrrolidin-2-yl}carbonyl)pyrrolidine-2-carbonitrile (compound 14)

The title compound was prepared in a manner similar to that described in Example 1.

¹H NMR (300 MHz, CD₃OD): δ 5.04-4.98 (m, 2H), 4.78 (t, J=5.4 Hz, 1H), 4.49 (dd, J=3.0, 8.7 Hz, 1H), 4.35-4.20 (m, 2H), 4.08-4.04 (m, 2H), 3.71-3.57 (m, 2H), 3.04-2.94 (m, 2H), 2.77-2.65 (m, 1H), 2.44-2.05 (m, 6H). MS (ES⁺) m/z calcd. for $C_{18}H_{20}F_3N_7O_3$: 439.16. found: 440.0 (M+H).

Example 15

Preparation of (3S,5S)-3-[2-(1,3-dihydro-2H-isoindol-2-yl)-2-oxoethyl]-5-(1,3-thiazolidin-3-ylcarbonyl)pyrrolidin-2-one (compound 15)

The title compound was prepared in a manner similar to that described in Example 1.

¹H NMR (300 MHz, CDCl₃): δ 7.30-7.26 (m, 4H), 6.96 (d, J=10.2 Hz, 1H), 4.82 (s, 2H), 4.77 (s, 2H), 4.66-4.40 (m, 3H), 3.94-3.67 (m, 2H), 3.11 (t, J=6.3 Hz, 1H), 3.03-2.93 (m, 2H), 2.60-2.46 (m, 2H), 2.40-2.30 (m, 2H). MS (ES⁺) m/z calcd. for $C_{18}H_{21}N_3O_3S$: 359.13. found: 360.1 (M+H).

Example 16

Preparation of (2S)-1-({(2S,4R)-4-[2-(1,3-dihydro-2H-isoindol-2-yl)-2-oxoethyl]-5-oxopyrrolidin-2-yl}carbonyl)pyrrolidine-2-carbonitrile (compound 16)

The title compound was prepared in a manner similar to that described in Example 1.

¹H NMR (400 MHz, CDCl₃): (6/1 mixture of trans/cis amide rotamers) δ 7.29-7.26 (m, 4H), 6.51 (s, 0.86H), 6.24 (s, 0.14H), 4.83-4.74 (m, 5H), 4.59-4.55 (m, 0.14H), 4.40-4.35 (m, 0.86H), 3.69-3.52 (m, 2H), 3.15-3.03 (m, 2H), 2.50-2.38 (m, 1H), 2.31-2.04 (m, 3H), 1.87-1.75 (m, 3H). MS (ES⁺) m/z calcd. for $C_{20}H_{22}N_4O_3$: 366.17. found: 367.1 (M+H).

Example 17

Preparation of (2S)-1-({(2S,4S)-4-[2-(5-fluoro-1,3-dihydro-2H-isoindol-2-yl)-2-oxo ethyl]-5-oxopyrrolidin-2-yl}carbonyl)pyrrolidine-2-carbonitrile (17)

The title compound was prepared in a manner similar to that described in Example 1.

¹H NMR (400 MHz, CDCl₃): (7/1 mixture of trans/cis amide rotamers) δ 7.24-7.19 (m, 1H), 7.02-6.95 (m, 2H), 6.70 (d, J=4.0 Hz, 0.88H), 6.18 (d, J=4.0 Hz, 0.12H), 4.83-4.72 (m, 4.88H), 4.61 (d, J=7.2 Hz, 0.12H), 4.51 (d, J=8.8 Hz, 0.12H), 4.39 (dd, J=2.8, 8.8 Hz, 0.88H), 3.69-3.52 (m, 2H), 2.98-2.87

(m, 2H), 2.61-2.39 (m, 3H), 2.30-2.17 (m, 4H). MS (ES+) m/z calcd. for $C_{20}H_{21}FN_4O_3$: 384.16. found: 385.3 (M+H).

Example 18

Preparation of (2S)-1-({(2S,4S)-4-[2-(5-trifluoromethyl-1,3-dihydro-2H-isoindol-2-yl)-2-oxo ethyl]-5-oxopyrrolidin-2-yl}carbonyl)pyrrolidine-2-carbonitrile (compound 18)

The title compound was prepared in a manner similar to that described in Example 1.

$^1$H NMR (300 MHz, $CDCl_3$): (7/1 mixture of trans/cis amide rotomers) δ 7.60-7.55 (m, 2H), 7.42 (t, J=7.5 Hz, 1H), 7.19 (d, J=4.2 Hz, 0.88H), 6.55 (d, J=4.2 Hz, 0.12H), 4.90-4.83 (m, overlapped two singlet at 4.90, 4.83, 4.88H), 4.69 (d, J=7.8 Hz, 0.12H), 4.56 (d, J=8.4 Hz, 0.12H), 4.65 (d, J=7.8 Hz, 0.88H), 3.64-3.60 (m, 2H), 3.09-2.91 (m, 2H), 2.63-2.20 (m, 7H). MS (ES+) m/z calcd. for $C_{21}H_{21}F_3N_4O_3$: 434.16. found: 435.0 (M+H).

Example 19

Bioassays

Expression and Purification of DPP-IV

DPP-IV was purified from healthy Asian human semen according to the method described in Chien C. et al. *J. Biol. Chem.*, 2004, 279: 52338-52345. The purity of the protein was assessed by SDS-PAGE, and the proteins were visualized by Commassie blue stain. The concentration of DPP-IV was measured by a well-established method using bovine serum albumin (BSA) as the standard (Bradford, M. M. (1976) *Anal. Biochem.* 72, 248-254).

Alternatively, recombinant DPP-IV was expressed and purified from Hi5 insect cells. See Chien C. et al. *J. Biol. Chem.*, 2004, 279: 52338-52345 and Chien C. et al., *Biochemistry* 2006, 45: 7006-7012. Briefly, the cDNA fragment coding for human DPP-IV was fused to the signal sequence of CD5 in-frame. The resultant CD5/DPP-IV construct was inserted into the expression vector pBac-PAC-His2 (Clontech) to generate a recombinant baculovirus. Hi5 insect cells, grown in serum-free medium (Express V), were infected with this recombinant virus at a multiplicity of infection (MOI) of 1.0 $TCID_{50}$ unit/cell ($TCID_{50}$: 50% tissue culture infectious dose) and then cultured for 72 hours before harvesting the secreted DPP-IV.

Expression and Purification of DPP-VIII

DPP-VIII was expressed and purified from Sf9 insect cells. Chen Y. et al., *Protein Expr Purif.* 2004, 35: 142-146 and Lee H. et al., *J. Biol. Chem.* 2006, 281: 38653-38662. Briefly, a full length human DPP-VIII cDNA was amplified from a human liver cDNA library by RT-PCR, and then cloned into the baculovirus expression vector pBac-PAC-His2 (Clontech). This vector was modified by inserting an MT-eGFP cassette at the EcoRV site to facilitate identification of recombinant baculovirus expressing the eGFP protein. Recombinant virus isolation was confirmed by fluorescent eGFP expression, enzyme activity, and the Western blot. The protein expression levels were checked at different MOIs. DPP-VIII expression was determined by the protease activity, which corresponded to the amounts of proteins expressed. Sf9 cells were infected at an MOI of 0.5 $TCDI_{50}$ U/cell and collected 72 hours later for subsequent protein purification.

Expression and Purification of DPP-II

Recombinant DPP-II protein was expressed and purified from Hi5 insect cells in a manner similar to that used to express and purify DPP-IV described above. DPP-II was purified by ConA-sepharose and Q-sepharose HP chromatography. The culturing medium was collected and then its pH value was adjusted to 7.4. It was then loaded onto a ConA-sepharose column, washed by 20 mM Tris, 500 mM NaCl, 1 mM $CaCl_2$, and 1 mM $MgCl_2$ at pH 7.4, and eluted by 250 mM methyl-mannopyranoside in 20 mM Tris and 500 mM NaCl at pH 7.4. The eluate was exchanged with a buffer containing 20 mM Tris at pH 7.4 using an Amicon YM-30 membrane (Millipore). After binding to a Q-sepharose HP column, DPP-II was eluted with a 0 to 200 mM NaCl gradient. The eluate was concentrated using an Amicon YM-30 membrane. The purity of the enzyme was determined by SDS-PAGE with Commassie blue staining and its concentration was determined by the above-mentioned Bradford method using BSA as the standard.

Expression and Purification of Human DPP-IX

Recombinant DPP-IX was expressed and purified from Sf9 insect cells in a manner similar to that used to express and purify DPP-VIII described above. Sf9 cells infected with baculovirus containing DPP-IX were pelleted and resuspended in binding buffer containing 150 mM NaCl, 100 mM Tris-HCl, 1 mM EDTA, pH 8.0. After sonication, the cell lysates were loaded onto a Strep Tactin® column (EMD Chemicals Inc., Darmstadt, Germany) and eluted with the binding buffer, followed by a buffer (pH 8.0) containing 150 mM NaCl, 100 mM Tris-HCl, 1 mM EDTA, and 2.5 mM desthiobiotin. The eluate was concentrated using Amicon with 10 kDa-cut membrane (Millipore, Billerica, Mass., USA). The purified DPP-IX was stored in at 10% glycerol −80° C.

Expression and Purification of FAP

FAP was expressed and purified from Hi5 insect cells in a manner similar to that used to express and purify DPP-IV described above.

$IC_{50}$ Determination

Compounds 1-18 were tested in this assay. For each test compound, a series of 100 µL-solutions containing 0.003-100 µM of the test compound and 1% DMSO, as well as the enzyme, substrate, and buffer system listed in the table below, were used.

|  | Substrate | Buffer system |
| --- | --- | --- |
| DPP-IV | 500 µM Gly-Pro-pNA* | 2 mM Tris-HCl, pH 8.0 |
| DPP-II | 1.5 mM Gly-Pro-pNA | PBS buffer, pH 5.5 |
| DPP-VIII | 2.5 mM Gly-Pro-pNA | PBS buffer, pH 8.0 |
| DPP-IX | 1.5 mM Gly-Pro-pNA | PBS buffer, pH 8.0 |
| FAP | 1.5 mM Ala-Pro-pNA* | PBS buffer, pH 8.0 |

*Enzyme substrates Gly-Pro-pNA and Ala-Pro-pNA were purchased from Bachem.

Enzyme activity (the amount of enzyme needed to cleave 1 µmol of the substrate per minute) was assayed continuously for 30 min at 37° C. using an ELISA reader at the emission of 405 nM according to the methods described in Jiaang W. et al., *Bioorg Med Chem Lett* 2005, 15: 687-691; Lu L. et al., *Bioorg Med Chem Lett* 2005, 15: 3271-3275; Tsai T. et al., *Bioorg Med Chem Lett* 2006, 16: 3268-3272; Tsu H. et al., *J Med Chem* 2006, 49: 373-380; and Coumar M. et al., *Bioorg Med Chem Lett* 2007, 17: 1274-1279.

$IC_{50}$ values were calculated for each enzyme by employing commercially available curve-fitting programs—SigmaPlot. The results show that almost all of tested compounds were effective in inhibiting FAP. Among them, Compounds 1-9, 11-14, 16-18, and 20 had $IC_{50}$ values lower than 20 µM and Compounds 1-9, 12, 13, 16-18, and 20 had $IC_{50}$ values lower than 1 µM. Moreover, some compounds were effective in inhibiting DPP-IV, DPP-VIII, DPP-IX, or DPP-II.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the diamide compounds of this invention also can be made, screened for their inhibitory activities against fibroblast activation protein and treating cancer or inflammation conditions and used to practice this invention. Thus, other embodiments are also within the claims.

What is claimed is:

1. A compound of the following formula:

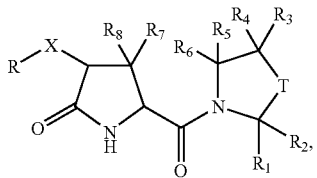

wherein
each of $R_1$, $R_2$, $R_3$, $R_4$, $R_5$, $R_6$, $R_7$, and $R_8$, independently, is H, halo, alkyl, cyano, nitro, amino, boronic acid, boronic ester, cycloalkyl, heterocycloalkyl, aryl, or heteroaryl;

T is $C(R_aR_b)$, $NR_c$, O, or S; in which each of $R_a$ and $R_b$, independently, is H, alkyl, halo, cyano, nitro, amino, alkoxy, hydroxy, cycloalkyl, heterocycloalkyl, aryl, or heteroaryl; and $R_c$ is H, alkyl, cycloalkyl, heterocycloalkyl, aryl, or heteroaryl;

X is $C(R_dR_e)$, $NR_f$, O, or S; in which each of $R_d$ and $R_e$, independently, is H, alkyl, halo, cyano, nitro, alkoxy, hydroxy, cycloalkyl, heterocycloalkyl, aryl, or heteroaryl; and $R_f$ is H, alkyl, cycloalkyl, heterocycloalkyl, aryl, or heteroaryl; and R is alkyl, cycloalkyl, heterocycloalkyl, aryl, heteroaryl, —C(O)OR$_g$, or —C(O)NR$_h$R$_i$; in which R$_g$ is alkyl, cycloalkyl, heterocycloalkyl, aryl, or heteroaryl; and each of R$_h$ and R$_i$, independently, is H, alkyl, cycloalkyl, heterocycloalkyl, aryl, heteroaryl, arylalkyl, or hydroxy, or R$_h$ and R$_i$ together with the N atom to which they are attached form a 5 or 6 membered ring, optionally substituted with alkyl, aryl, halo, hydroxy, alkoxy, nitro, amino, alkoxycarbonyl, or carboxy; and optionally fused with a 3-8 membered aromatic or non-aromatic ring containing 0, 1, 2, or 3 heteroatoms.

2. The compound of claim 1, wherein R is —C(O)NR$_h$R$_i$; R$_h$ and R$_i$ together with the N atom to which they are attached form a 5 or 6 membered ring, optionally substituted with alkyl, aryl, halo, hydroxy, alkoxy, nitro, amino, alkoxycarbonyl, or carboxy; and optionally fused with a 3-8 membered aromatic or non-aromatic ring containing 0, 1, 2, or 3 heteroatoms.

3. The compound of claim 1, wherein R is —C(O)NR$_h$R$_i$; each of R$_h$ and R$_i$, independently, is H, alkyl, cycloalkyl, heterocycloalkyl, aryl, heteroaryl, arylalkyl, or hydroxyl hydroxy.

4. The compound of claim 1, wherein T is S.

5. The compound of claim 1, wherein $R_1$ is CN.

6. The compound of claim 1, wherein the compound is

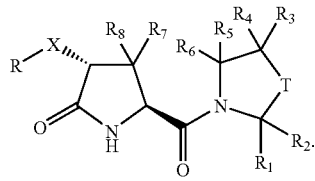

7. The compound of claim 1, wherein R is —C(O)OR$_g$ or —C(O)NR$_h$R$_i$; in which R$_g$ is alkyl, cycloalkyl, heterocycloalkyl, aryl, or heteroaryl; and each of R$_h$ and independently, is H, alkyl, cycloalkyl, heterocycloalkyl, aryl, heteroaryl, arylalkyl, or hydroxy, or R$_h$ and R$_i$ together with the N atom to which they are attached form a 5 or 6 membered ring, optionally substituted with alkyl, aryl, halo, hydroxy, alkoxy, nitro, amino, alkoxycarbonyl, or carboxy; and optionally fused with a 3-8 membered aromatic or non-aromatic ring containing 0, 1, 2, or 3 heteroatoms.

8. The compound of claim 7, wherein X is CH$_2$.

9. The compound of claim 8, wherein T is CH$_2$.

10. The compound of claim 9, wherein R is —C(O)NR$_h$R$_i$; R$_h$ and R$_i$ together with the N atom to which they are attached form a 5 or 6 membered ring, optionally substituted with alkyl, aryl, halo, hydroxy, alkoxy, nitro, amino, alkoxycarbonyl, or carboxy; and optionally fused with a 3-8 membered aromatic or non-aromatic ring containing 0, 1, 2, or 3 heteroatoms.

11. The compound of claim 10, wherein $R_1$ is CN.

12. The compound of claim 1, wherein T is CH$_2$.

13. The compound of claim 12, wherein $R_1$ is CN.

14. The compound of claim 13, wherein R is —C(O)NR$_h$R$_i$; R$_h$ and R$_i$ together with the N atom to which they are attached form a 5 or 6 membered ring, optionally substituted with alkyl, aryl, halo, hydroxy, alkoxy, nitro, amino, alkoxycarbonyl, or carboxy; and optionally fused with a 3-8 membered aromatic or non-aromatic ring containing 0, 1, 2, or 3 heteroatoms.

15. The compound of claim 14, wherein $R_1$ is CN.

16. The compound of claim 15, wherein R is —C(O)NR$_h$R$_i$; R$_h$ and R$_i$ together with the N atom to which they are attached form a 5 or 6 membered ring, optionally substituted with alkyl, aryl, halo, hydroxy, alkoxy, nitro, amino, alkoxycarbonyl, or carboxy; and optionally fused with a 3-8 membered aromatic or non-aromatic ring containing 0, 1, 2, or 3 heteroatoms.

17. The compound of claim 1, wherein the compound is selected from a group consisting of

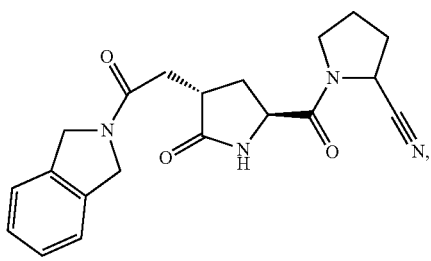

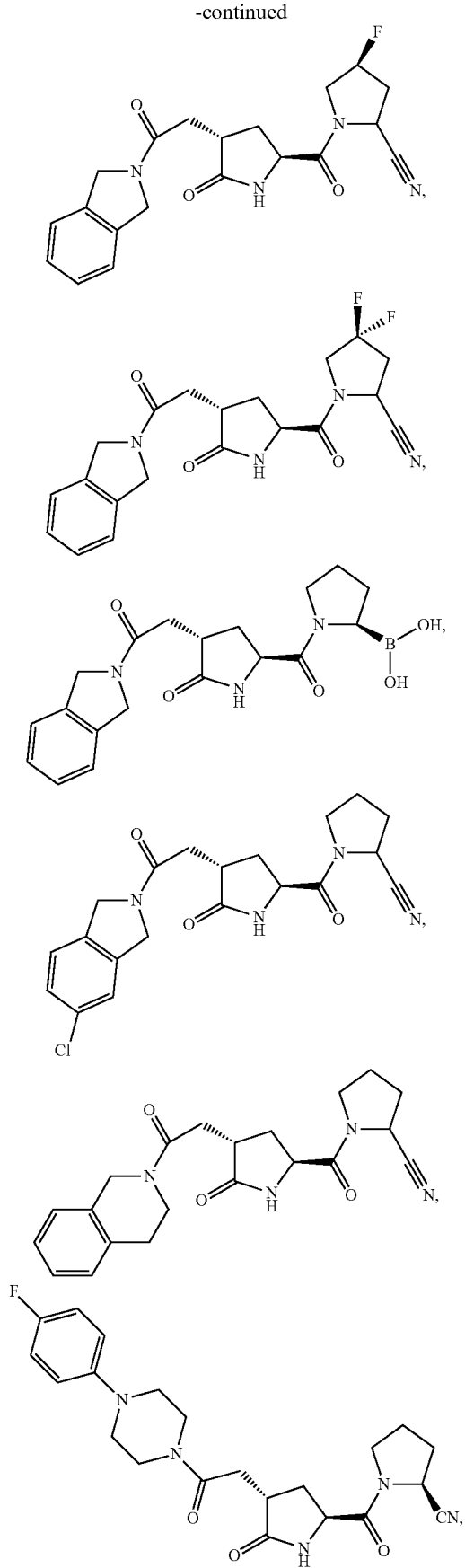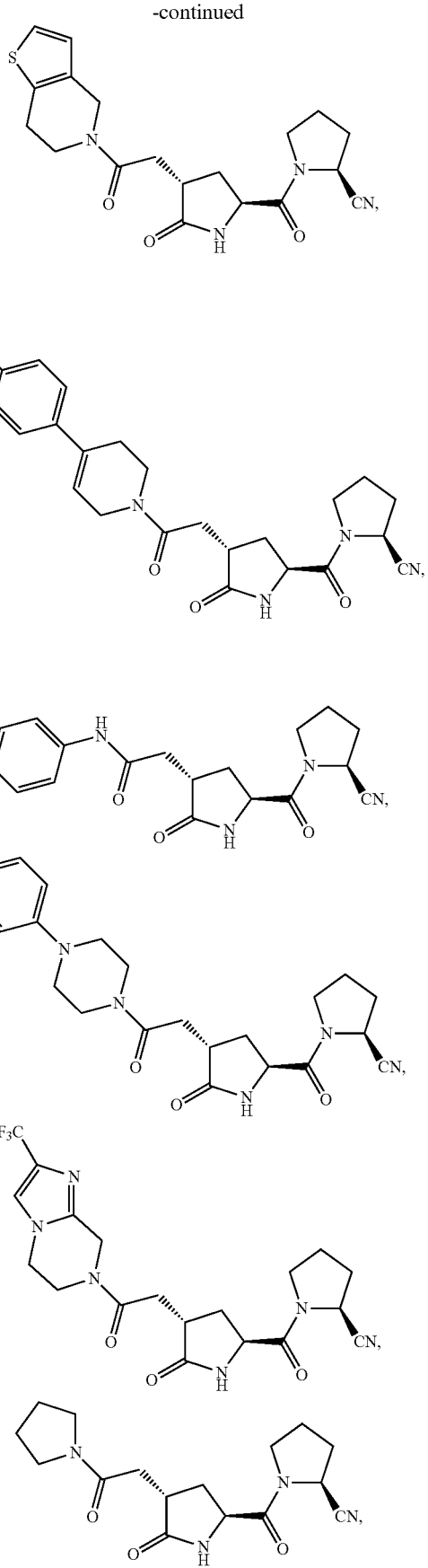

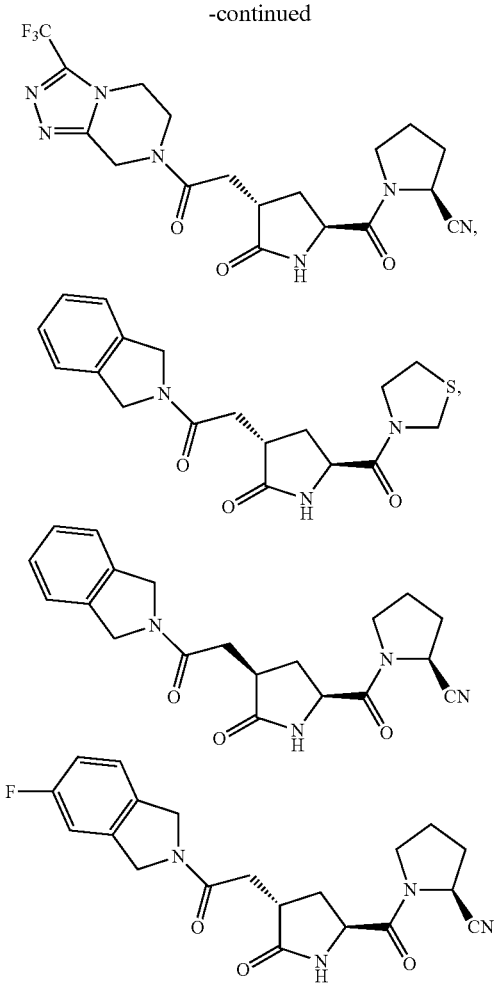
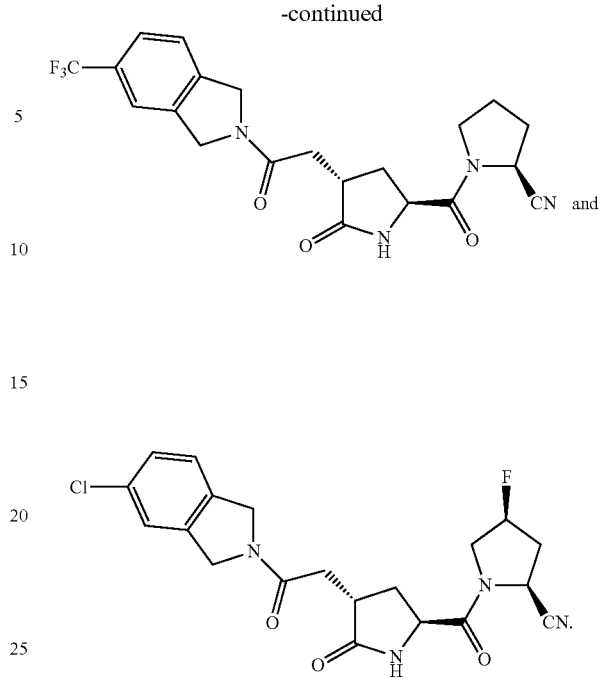
18. A method of inhibiting activity of dipeptidyl peptidase, comprising contacting the fibroblast activation protein with an effective amount of a compound of claim 1.
19. The method of claim 18, wherein the dipeptidyl peptidase is FAP or DPP-IV.
* * * * *